(12) United States Patent
Schwemberger

(10) Patent No.: US 7,837,080 B2
(45) Date of Patent: Nov. 23, 2010

(54) SURGICAL STAPLING INSTRUMENT WITH DEVICE FOR INDICATING WHEN THE INSTRUMENT HAS CUT THROUGH TISSUE

(75) Inventor: Richard F. Schwemberger, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 163 days.

(21) Appl. No.: 12/212,928

(22) Filed: Sep. 18, 2008

(65) Prior Publication Data
US 2010/0065609 A1   Mar. 18, 2010

(51) Int. Cl.
*A61B 17/64* (2006.01)
(52) U.S. Cl. .................. 227/176.1; 227/175.1; 606/143
(58) Field of Classification Search ... 227/175.1–182.1; 606/48, 50, 51, 139, 142, 143
See application file for complete search history.

(56) References Cited

U.S. PATENT DOCUMENTS

| | | | |
|---|---|---|---|
| 2,853,074 | A | 9/1958 | Olson |
| 3,551,987 | A | 1/1971 | Wilkinson |
| 4,429,695 | A | 2/1984 | Green |
| 4,506,671 | A | 3/1985 | Green |
| 4,619,262 | A | 10/1986 | Taylor |
| 4,809,695 | A | 3/1989 | Gwathmey et al. |
| 5,104,025 | A | 4/1992 | Main et al. |
| 5,205,459 | A | 4/1993 | Brinkerhoff et al. |
| 5,222,963 | A | 6/1993 | Brinkerhoff et al. |
| 5,275,322 | A | 1/1994 | Brinkerhoff et al. |
| 5,285,945 | A | 2/1994 | Brinkerhoff et al. |
| 5,309,927 | A | 5/1994 | Welch |
| 5,395,033 | A * | 3/1995 | Byrne et al. ............. 227/175.1 |
| 5,403,312 | A | 4/1995 | Yates et al. |
| 5,417,361 | A | 5/1995 | Williamson, IV |
| 5,433,721 | A * | 7/1995 | Hooven et al. ............. 606/143 |
| 5,480,089 | A | 1/1996 | Blewett |
| 5,482,197 | A | 1/1996 | Green et al. |
| 5,484,095 | A | 1/1996 | Green et al. |
| 5,485,947 | A | 1/1996 | Olson et al. |
| 5,485,952 | A | 1/1996 | Fontayne |
| 5,487,499 | A | 1/1996 | Sorrentino et al. |
| 5,487,500 | A | 1/1996 | Knodel et al. |
| 5,489,058 | A | 2/1996 | Plyley et al. |
| 5,497,933 | A | 3/1996 | DeFonzo et al. |

(Continued)

FOREIGN PATENT DOCUMENTS

CA   2458946 A1   3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner*—Paul R Durand

(57) ABSTRACT

Circular stapling instruments for cutting and applying one or more surgical staples to tissue are disclosed. The instruments include various forms of feedback systems designed to provide at least one mode of feedback to the surgeon when the knife has cut through tissue clamped between a staple cartridge and an anvil portion.

22 Claims, 11 Drawing Sheets

U.S. PATENT DOCUMENTS

| | | | |
|---|---|---|---|
| 5,503,320 A | 4/1996 | Webster et al. | |
| 5,509,596 A | 4/1996 | Green et al. | |
| 5,529,235 A | 6/1996 | Boiarski et al. | |
| 5,535,934 A | 7/1996 | Boiarski et al. | |
| 5,535,937 A * | 7/1996 | Boiarski et al. | 227/175.3 |
| 5,540,375 A | 7/1996 | Bolanos et al. | |
| 5,542,594 A | 8/1996 | McKean et al. | |
| 5,553,765 A | 9/1996 | Knodel et al. | |
| 5,560,530 A | 10/1996 | Bolanos et al. | |
| 5,560,532 A | 10/1996 | DeFonzo et al. | |
| 5,562,241 A | 10/1996 | Knodel et al. | |
| 5,564,615 A | 10/1996 | Bishop et al. | |
| 5,577,654 A | 11/1996 | Bishop | |
| 5,580,067 A | 12/1996 | Hamblin et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,601,224 A | 2/1997 | Bishop et al. | |
| 5,603,443 A | 2/1997 | Clark et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,609,285 A | 3/1997 | Grant et al. | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,632,433 A | 5/1997 | Grant et al. | |
| 5,634,584 A | 6/1997 | Okorocha et al. | |
| 5,636,780 A | 6/1997 | Green et al. | |
| 5,639,008 A | 6/1997 | Gallagher et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,667,517 A * | 9/1997 | Hooven | 606/151 |
| 5,669,544 A | 9/1997 | Schulze et al. | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,685,474 A | 11/1997 | Seeber | |
| 5,688,270 A | 11/1997 | Yates et al. | |
| 5,690,269 A | 11/1997 | Bolanos et al. | |
| 5,692,668 A | 12/1997 | Schulze et al. | |
| 5,693,042 A * | 12/1997 | Boiarski et al. | 606/10 |
| 5,697,543 A | 12/1997 | Burdorff | |
| 5,704,534 A | 1/1998 | Huitema et al. | |
| 5,709,680 A | 1/1998 | Yates et al. | |
| 5,711,472 A | 1/1998 | Bryan | |
| 5,713,505 A | 2/1998 | Huitema | |
| 5,715,987 A | 2/1998 | Kelley et al. | |
| 5,732,871 A | 3/1998 | Clark et al. | |
| 5,732,872 A | 3/1998 | Bolduc et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,256 A | 6/1998 | Mastri et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,397 A * | 7/1998 | Koukline | 227/176.1 |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,799,857 A | 9/1998 | Robertson et al. | |
| 5,810,811 A | 9/1998 | Yates et al. | |
| 5,817,093 A | 10/1998 | Williamson, IV et al. | |
| 5,820,009 A | 10/1998 | Melling et al. | |
| 5,826,776 A | 10/1998 | Schulze et al. | |
| 5,829,662 A | 11/1998 | Allen et al. | |
| 5,836,503 A | 11/1998 | Ehrenfels et al. | |
| 5,839,639 A | 11/1998 | Sauer et al. | |
| 5,855,311 A | 1/1999 | Hamblin et al. | |
| 5,865,361 A | 2/1999 | Milliman et al. | |
| 5,871,135 A | 2/1999 | Williamson, IV et al. | |
| 5,876,401 A | 3/1999 | Schulze et al. | |
| 5,901,895 A | 5/1999 | Heaton et al. | |
| 5,911,353 A | 6/1999 | Bolanos et al. | |
| 5,915,616 A | 6/1999 | Viola et al. | |
| 5,941,442 A | 8/1999 | Geiste et al. | |
| 5,954,259 A | 9/1999 | Viola et al. | |
| 6,010,054 A | 1/2000 | Johnson et al. | |
| 6,032,849 A | 3/2000 | Mastri et al. | |
| 6,102,271 A | 8/2000 | Longo et al. | |
| 6,119,913 A | 9/2000 | Adams et al. | |
| H1904 H | 10/2000 | Yates et al. | |
| 6,126,058 A | 10/2000 | Adams et al. | |
| 6,202,914 B1 | 3/2001 | Geiste et al. | |
| 6,241,139 B1 | 6/2001 | Milliman et al. | |
| 6,241,723 B1 * | 6/2001 | Heim et al. | 606/34 |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,330,965 B1 | 12/2001 | Milliman et al. | |
| 6,488,197 B1 | 12/2002 | Whitman | |
| 6,491,201 B1 | 12/2002 | Whitman | |
| 6,505,768 B2 | 1/2003 | Whitman | |
| 6,578,751 B2 | 6/2003 | Hartwick | |
| 6,588,643 B2 | 7/2003 | Bolduc et al. | |
| 6,601,749 B2 | 8/2003 | Sullivan et al. | |
| 6,619,529 B2 | 9/2003 | Green et al. | |
| 6,644,532 B2 | 11/2003 | Green et al. | |
| 6,681,978 B2 | 1/2004 | Geiste et al. | |
| 6,681,979 B2 | 1/2004 | Whitman | |
| 6,682,528 B2 | 1/2004 | Frazier et al. | |
| 6,695,199 B2 | 2/2004 | Whitman | |
| 6,698,643 B2 | 3/2004 | Whitman | |
| 6,752,816 B2 * | 6/2004 | Culp et al. | 606/170 |
| 6,755,338 B2 | 6/2004 | Hahnen et al. | |
| 6,786,382 B1 | 9/2004 | Hoffman | |
| 6,805,273 B2 | 10/2004 | Bilotti et al. | |
| 6,817,508 B1 | 11/2004 | Racenet et al. | |
| 6,817,509 B2 | 11/2004 | Geiste et al. | |
| 6,830,174 B2 | 12/2004 | Hillstead et al. | |
| 6,843,403 B2 | 1/2005 | Whitman | |
| RE38,708 E | 3/2005 | Bolanos et al. | |
| 6,874,669 B2 | 4/2005 | Adams et al. | |
| 6,877,647 B2 | 4/2005 | Green et al. | |
| 6,905,057 B2 | 6/2005 | Swayze et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,986,451 B1 | 1/2006 | Mastri et al. | |
| 6,988,650 B2 | 1/2006 | Schwemberger et al. | |
| 7,000,818 B2 | 2/2006 | Shelton, IV et al. | |
| 7,000,819 B2 | 2/2006 | Swayze et al. | |
| 7,032,798 B2 | 4/2006 | Whitman et al. | |
| 7,032,799 B2 | 4/2006 | Viola et al. | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |

| Patent/Publication | Date | Name |
|---|---|---|
| 7,070,083 B2 | 7/2006 | Jankowski |
| 7,077,856 B2 * | 7/2006 | Whitman .................... 606/219 |
| 7,080,769 B2 | 7/2006 | Vresh et al. |
| 7,083,075 B2 | 8/2006 | Swayze et al. |
| 7,090,673 B2 | 8/2006 | Dycus et al. |
| 7,111,769 B2 | 9/2006 | Wales et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,160,299 B2 | 1/2007 | Baily |
| 7,168,604 B2 | 1/2007 | Milliman et al. |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,225,964 B2 | 6/2007 | Mastri et al. |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,481,347 B2 | 1/2009 | Roy |
| 7,494,039 B2 | 2/2009 | Racenet et al. |
| 7,506,790 B2 | 3/2009 | Shelton, IV |
| 7,510,107 B2 | 3/2009 | Timm et al. |
| 7,546,940 B2 | 6/2009 | Milliman et al. |
| 7,549,564 B2 | 6/2009 | Boudreaux |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,631,793 B2 | 12/2009 | Rethy et al. |
| 7,658,311 B2 | 2/2010 | Boudreaux |
| 7,665,646 B2 | 2/2010 | Prommersberger |
| 7,669,747 B2 | 3/2010 | Weisenburgh, II et al. |
| 7,673,782 B2 | 3/2010 | Hess et al. |
| 2002/0117534 A1 | 8/2002 | Green et al. |
| 2002/0165541 A1 | 11/2002 | Whitman |
| 2004/0094597 A1 | 5/2004 | Whitman et al. |
| 2004/0108357 A1 | 6/2004 | Milliman et al. |
| 2004/0149802 A1 * | 8/2004 | Whitman .................... 227/180.1 |
| 2004/0164123 A1 | 8/2004 | Racenet et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2005/0103819 A1 | 5/2005 | Racenet et al. |
| 2005/0184121 A1 | 8/2005 | Heinrich |
| 2005/0189397 A1 | 9/2005 | Jankowski |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0049229 A1 | 3/2006 | Milliman et al. |
| 2006/0108393 A1 | 5/2006 | Heinrich et al. |
| 2006/0180634 A1 | 8/2006 | Shelton, IV et al. |
| 2006/0226196 A1 | 10/2006 | Hueil et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0045379 A1 | 3/2007 | Shelton, IV |
| 2007/0073340 A1 | 3/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0173813 A1 | 7/2007 | Odom |
| 2007/0175949 A1 * | 8/2007 | Shelton et al. .......... 227/176.1 |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |

| | | | |
|---|---|---|---|
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0251568 A1 | 10/2008 | Zemlok et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314955 A1 | 12/2008 | Boudreaux et al. |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2009/0292283 A1 | 11/2009 | Odom |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |

| | | | | | | |
|---|---|---|---|---|---|---|
| EP | 1256318 | B1 | 5/2001 | JP | 2002369820 A | 12/2002 |
| EP | 0908152 | B1 | 1/2002 | JP | 2005505322 T | 2/2005 |
| EP | 0872213 | B1 | 5/2002 | JP | 2005103293 A | 4/2005 |
| EP | 1238634 | A2 | 9/2002 | RU | 2187249 C2 | 8/2002 |
| EP | 0656188 | B1 | 1/2003 | RU | 2225170 C2 | 3/2004 |
| EP | 0829235 | B1 | 6/2003 | SU | 1377053 A1 | 2/1988 |
| EP | 0813843 | B1 | 10/2003 | SU | 1561964 A1 | 5/1990 |
| EP | 0741996 | B1 | 2/2004 | SU | 1722476 A1 | 3/1992 |
| EP | 0705570 | B1 | 4/2004 | WO | WO 93/08755 A1 | 5/1993 |
| EP | 1086713 | B1 | 5/2004 | WO | WO 95/18572 A1 | 7/1995 |
| EP | 1426012 | A1 | 6/2004 | WO | WO 95/23557 A1 | 9/1995 |
| EP | 0888749 | B1 | 9/2004 | WO | WO 95/29639 A1 | 11/1995 |
| EP | 1477119 | A1 | 11/2004 | WO | WO 96/22055 A1 | 7/1996 |
| EP | 1479345 | A1 | 11/2004 | WO | WO 96/35464 A1 | 11/1996 |
| EP | 1479347 | A1 | 11/2004 | WO | WO 97/34533 A1 | 9/1997 |
| EP | 1479348 | A1 | 11/2004 | WO | WO 97/39688 A2 | 10/1997 |
| EP | 1520521 | A1 | 4/2005 | WO | WO 98/17180 A1 | 4/1998 |
| EP | 1520523 | A1 | 4/2005 | WO | WO 98/30153 A1 | 7/1998 |
| EP | 1520525 | A1 | 4/2005 | WO | WO 99/12483 A1 | 3/1999 |
| EP | 1522264 | A1 | 4/2005 | WO | WO 99/15086 A1 | 4/1999 |
| EP | 1550408 | A1 | 7/2005 | WO | WO 99/34744 A1 | 7/1999 |
| EP | 1557129 | A1 | 7/2005 | WO | WO 99/45849 A1 | 9/1999 |
| EP | 1064883 | B1 | 8/2005 | WO | WO 00/24322 A1 | 5/2000 |
| EP | 1157666 | B1 | 9/2005 | WO | WO 00/57796 A1 | 10/2000 |
| EP | 1621138 | A2 | 2/2006 | WO | WO 00/64365 A1 | 11/2000 |
| EP | 1621139 | A2 | 2/2006 | WO | WO 00/72762 A1 | 12/2000 |
| EP | 1621141 | A2 | 2/2006 | WO | WO 00/72765 A1 | 12/2000 |
| EP | 1621145 | A2 | 2/2006 | WO | WO 01/05702 A1 | 1/2001 |
| EP | 1652481 | A2 | 5/2006 | WO | WO 01/10482 A1 | 2/2001 |
| EP | 1382303 | B1 | 6/2006 | WO | WO 01/54594 A1 | 8/2001 |
| EP | 1045672 | B1 | 8/2006 | WO | WO 01/62158 A2 | 8/2001 |
| EP | 1617768 | B1 | 8/2006 | WO | WO 01/62162 A1 | 8/2001 |
| EP | 1702567 | A2 | 9/2006 | WO | WO 01/62164 A2 | 8/2001 |
| EP | 1129665 | B1 | 11/2006 | WO | WO 01/91646 A1 | 12/2001 |
| EP | 1256317 | B1 | 12/2006 | WO | WO 02/07608 A2 | 1/2002 |
| EP | 1728473 | A1 | 12/2006 | WO | WO 02/07618 A1 | 1/2002 |
| EP | 1728475 | A2 | 12/2006 | WO | WO 02/17799 A1 | 3/2002 |
| EP | 1479346 | B1 | 1/2007 | WO | WO 02/19920 A1 | 3/2002 |
| EP | 1484024 | B1 | 1/2007 | WO | WO 02/30297 A2 | 4/2002 |
| EP | 1754445 | A2 | 2/2007 | WO | WO 02/32322 A2 | 4/2002 |
| EP | 1759812 | A1 | 3/2007 | WO | WO 02/43571 A2 | 6/2002 |
| EP | 1769756 | A1 | 4/2007 | WO | WO 02/058568 A1 | 8/2002 |
| EP | 1769758 | A1 | 4/2007 | WO | WO 02/060328 A1 | 8/2002 |
| EP | 1785097 | A2 | 5/2007 | WO | WO 02/067785 A2 | 9/2002 |
| EP | 1790293 | A2 | 5/2007 | WO | WO 02/098302 A1 | 12/2002 |
| EP | 1300117 | B1 | 8/2007 | WO | WO 03/000138 A2 | 1/2003 |
| EP | 1813199 | A1 | 8/2007 | WO | WO 03/001329 A2 | 1/2003 |
| EP | 1813201 | A1 | 8/2007 | WO | WO 03/013363 A1 | 2/2003 |
| EP | 1813203 | A2 | 8/2007 | WO | WO 03/020106 A2 | 3/2003 |
| EP | 1813207 | A1 | 8/2007 | WO | WO 03/020139 A2 | 3/2003 |
| EP | 1813209 | A1 | 8/2007 | WO | WO 03/079909 A3 | 3/2003 |
| EP | 1839596 | A1 | 10/2007 | WO | WO 03/030743 A2 | 4/2003 |
| EP | 1872727 | A1 | 1/2008 | WO | WO 03/037193 A1 | 5/2003 |
| EP | 1897502 | A1 | 3/2008 | WO | WO 03/047436 A3 | 6/2003 |
| EP | 1702568 | B1 | 7/2008 | WO | WO 03/057048 A1 | 7/2003 |
| EP | 1980213 | A2 | 10/2008 | WO | WO 03/057058 A1 | 7/2003 |
| EP | 1759645 | B1 | 11/2008 | WO | WO 03/063694 A1 | 8/2003 |
| EP | 1693008 | B1 | 12/2008 | WO | WO 03/077769 A1 | 9/2003 |
| EP | 1749486 | B1 | 3/2009 | WO | WO 03/082126 A1 | 10/2003 |
| EP | 2090256 | A2 | 8/2009 | WO | WO 03/088845 A2 | 10/2003 |
| EP | 1813206 | B1 | 4/2010 | WO | WO 03/090630 A2 | 11/2003 |
| FR | 999646 | A | 2/1952 | WO | WO 03/094743 A1 | 11/2003 |
| FR | 1112936 | A | 3/1956 | WO | WO 03/094745 A1 | 11/2003 |
| FR | 2765794 | A | 1/1999 | WO | WO 03/094746 A1 | 11/2003 |
| GB | 939929 | A | 10/1963 | WO | WO 03/094747 A1 | 11/2003 |
| GB | 1210522 | A | 10/1970 | WO | WO 03/101313 A1 | 12/2003 |
| GB | 2336214 | A | 10/1999 | WO | WO 03/105698 A2 | 12/2003 |
| JP | 6007357 | A | 1/1994 | WO | WO 03/105702 A2 | 12/2003 |
| JP | 7051273 | A | 2/1995 | WO | WO 2004/006980 A2 | 1/2004 |
| JP | 8033641 | A | 2/1996 | WO | WO 2004/028585 A2 | 4/2004 |
| JP | 8229050 | A | 9/1996 | WO | WO 2004/032754 A2 | 4/2004 |
| JP | 2000287987 | A | 10/2000 | WO | WO 2004/032760 A2 | 4/2004 |
| JP | 2001286477 | A | 10/2001 | WO | WO 2004/032762 A1 | 4/2004 |

| | | |
|---|---|---|
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

* cited by examiner

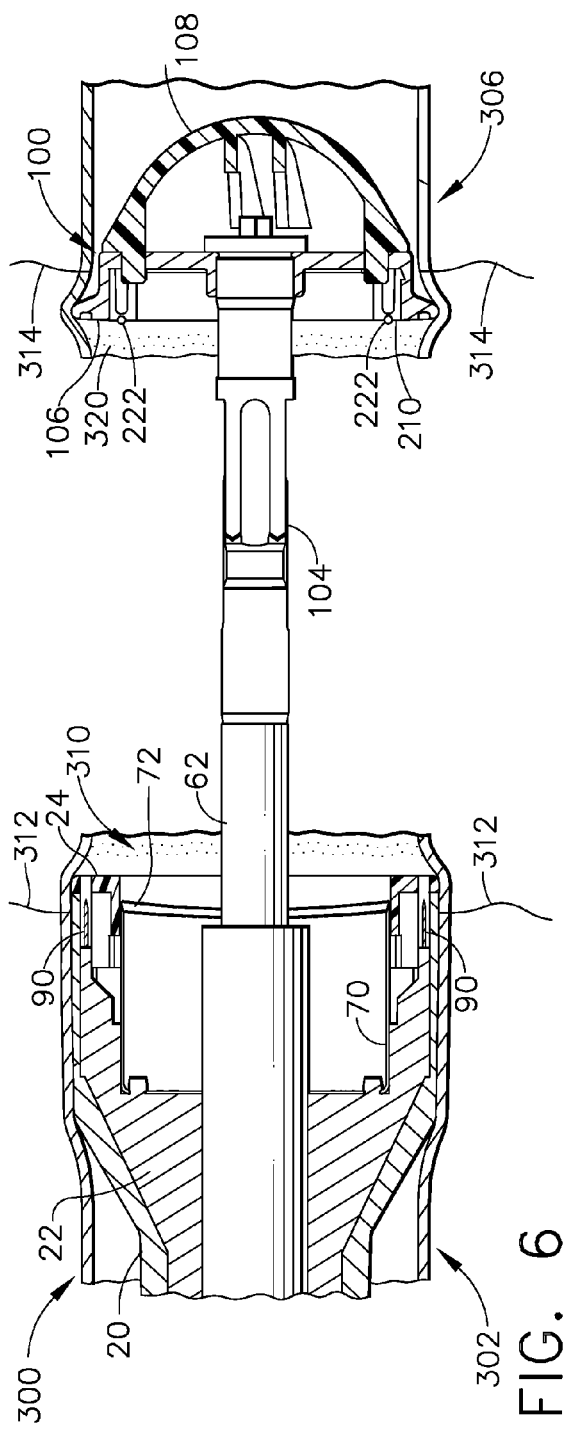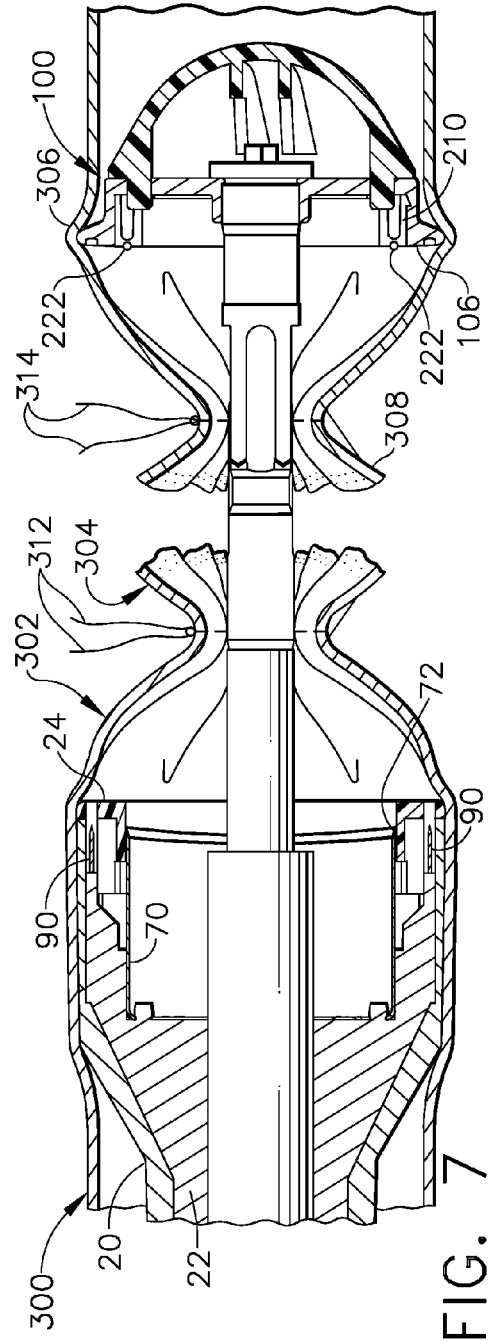

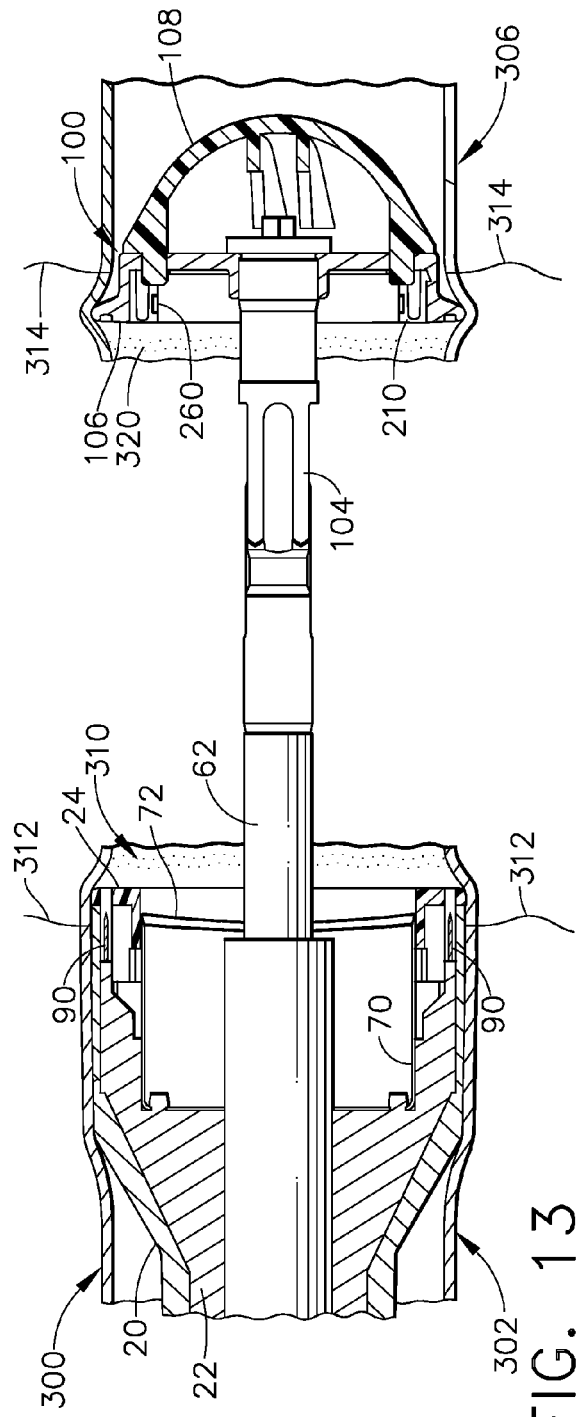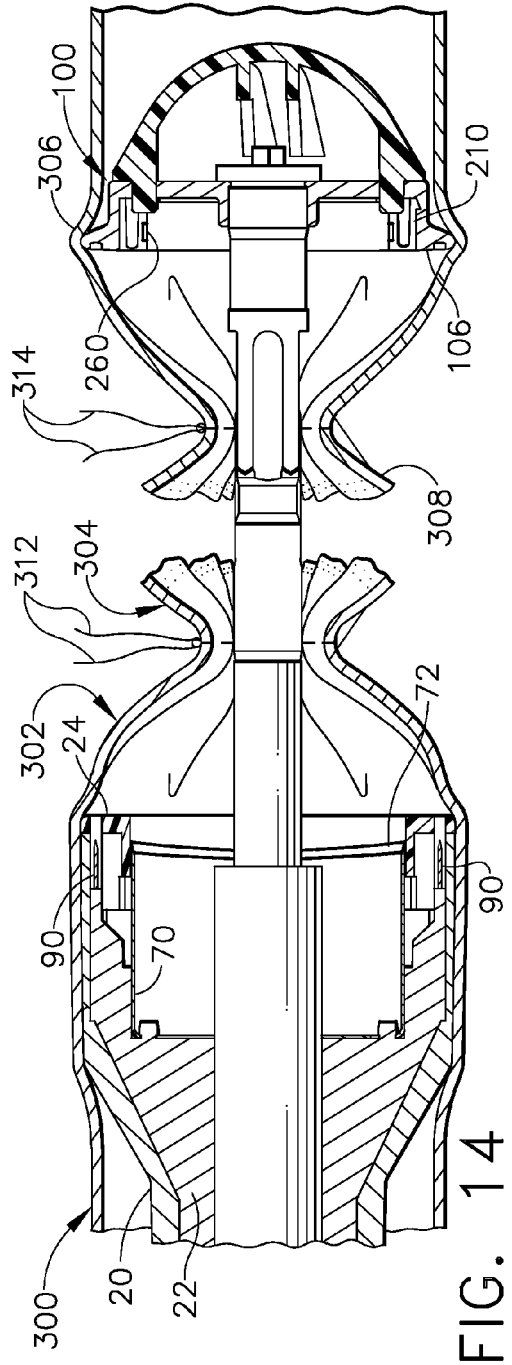

SURGICAL STAPLING INSTRUMENT WITH DEVICE FOR INDICATING WHEN THE INSTRUMENT HAS CUT THROUGH TISSUE

FIELD OF THE INVENTION

The present invention generally relates to surgical staplers, and more particularly, to circular stapling instruments for performing anastomosis stapling operations.

BACKGROUND

In certain types of surgical procedures, the use of surgical staples has become the preferred method of joining tissue and, as such, specially configured surgical staplers have been developed for these applications. For example, intra-luminal or circular staplers have been developed for use in a surgical procedure known as an anastomosis. Circular staplers useful for performing an anastomosis are disclosed, for example, in U.S. Pat. Nos. 5,104,025; 5,205,459; 5,285,945; and 5,309,927 which are each herein incorporated by reference in their respective entireties.

One form of an anastomosis comprises a surgical procedure wherein sections of intestine are joined together after a connecting section has been excised. The procedure requires joining the ends of two tubular sections together to form a continuous tubular pathway. Previously, this surgical procedure was a laborious and time consuming operation. The surgeon had to precisely cut and align the ends of the intestine and maintain the alignment while joining the ends with numerous suture stitches. The development of circular staplers has greatly simplified the anastomosis procedure and also decreased the time required to perform an anastomosis.

In general, a conventional circular stapler typically consists of an elongated shaft that has a proximal actuating mechanism and a distal stapling mechanism mounted to the shaft. The distal stapling mechanism typically consists of a fixed stapling cartridge containing a plurality of staples configured in a concentric circular array. A round cutting knife is concentrically mounted in the cartridge interior to the staples. The knife is moveable in an axial, distal direction. Extending axially from the center of the cartridge is a trocar shaft that has a staple anvil removably coupled thereto. The trocar shaft is moveable, axially, with respect to the cartridge and elongated shaft. The anvil is configured to form the ends of the staples as they are driven into it. The distance between a distal face of the staple cartridge and the staple anvil is controlled by an adjustment mechanism mounted to the proximal end of the stapler shaft. Tissue contained between the staple cartridge and the staple anvil is simultaneously stapled and cut when the actuating mechanism is activated by the surgeon.

When performing an anastomosis using a circular stapler, the intestine is typically stapled using a conventional surgical stapler with double rows of staples being emplaced on either side of a target section (i.e., specimen) of intestine. The target section is simultaneously cut as the section is stapled. After removing the specimen, the surgeon typically inserts the anvil into the proximal end of the lumen, proximal of the staple line. This is done by inserting the anvil head into an entry port cut into the proximal lumen by the surgeon. On occasion, the anvil can be placed transanally, by placing the anvil head on the distal end of the stapler and inserting the instrument through the rectum. The surgeon then ties the proximal end of the intestine to the anvil shaft using a suture or other conventional tying device. Next, the surgeon cuts excess tissue adjacent to the tie and the surgeon attaches the anvil to the trocar shaft of the stapler. The surgeon then closes the gap between the anvil and cartridge, thereby engaging the proximal and distal ends of the intestine in the gap. The surgeon next actuates the stapler causing several rows of staples to be driven through both ends of the intestine and formed, thereby joining the ends and forming a tubular pathway. Simultaneously, as the staples are driven and formed, the concentric circular knife blade is driven through the intestinal tissue ends, cutting the ends adjacent to the inner row of staples. The surgeon then withdraws the stapler from the intestine and the anastomosis is complete.

During the stapling process, however, it is often difficult for the surgeon to determine exactly when the knife blade has cut completely through the tissue. In an effort to provide the surgeon with some form of feedback concerning the travel of the knife, some prior staplers were fitted with a plastic washer or knife board designed to provide a "crunching" sound when the knife blade has traversed through the tissue to contact and breakthrough the washer. Often times, however, such feedback is insufficient.

Accordingly there is a need for an circular surgical stapler that has an improved system for providing an indication that the circular knife has completely cut through tissue.

BRIEF SUMMARY

The invention overcomes the above-noted and other deficiencies of the prior art by providing a surgical stapling instrument for applying one or more surgical staples to tissue. One form of the surgical instrument comprises a handle assembly and a stapling head assembly that is operably coupled to the handle assembly by a shaft assembly. In various embodiments, the instrument may include a staple cartridge for supporting one or more surgical staples and an anvil for clamping the tissue against the staple cartridge. A staple driver assembly may be provided for engaging and driving the staples from the staple cartridge into the tissue and against the anvil. A knife is movably supported in the stapling head assembly for cutting through the clamped tissue. A drive system is provided for selectively applying drive motions to the staple driver assembly and the knife. The instrument further includes a feedback system that comprises at least one sensor that is configured to transmit a signal to an indicator when the knife has cut through the clamped tissue.

In another general aspect of the present invention, there is provided a surgical stapling instrument for applying one or more surgical staples to tissue. In various embodiments, the instrument includes a handle assembly and a stapling head assembly that is operably coupled to the handle assembly by a shaft assembly. The stapling head assembly may comprise a staple cartridge for supporting one or more surgical staples and an anvil for clamping the tissue against the staple cartridge. A staple driver is provided for engaging and driving the staples from the staple cartridge into the tissue and against the anvil. A knife is movably supported in the stapling head assembly for cutting through the clamped tissue. A drive system is provided for applying drive motions to the staple driver and the knife. A feedback system is also provided. In various embodiments, the feedback system may comprise a knife board that is mounted in the anvil. The knife board may have at least one sensor operably supported therein for detecting the presence of the knife after the knife has cut through the clamped tissue. The sensor operably communicates with an indicator supported by the handle assembly such that when the knife has cut through the clamped tissue, the sensor permits the indicator to be energized.

In accordance with another general form of the present invention, there is provided a surgical stapling instrument for applying one or more surgical staples to tissue. In various embodiments, the surgical instrument comprises a handle assembly and a stapling head assembly. The stapling head assembly may include a staple cartridge for operably supporting a plurality of staples therein and a staple driver for engaging and driving staples from the staple cartridge. A knife is movably supported in the stapling head assembly. A drive system is also provided for applying drive motions to the staple driver and the knife. A shaft assembly may be operably coupled to the handle assembly and the stapling head assembly. The shaft assembly may include a selectively movable trocar. An anvil may be detachably mounted to the trocar and positioned relative to the stapling head assembly such that at least some of the tissue may be clamped between the staple cartridge and the anvil. The surgical instrument may further include a feedback system that comprises at least one sensor supported by the anvil and operably communicating with an indicator supported by the handle assembly such that when the knife has cut through the clamped tissue, the sensor permits the indicator to be energized.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 6 is a partial cross-sectional view showing the stapler of FIGS. 1-4 in the open position inserted into an intestine after a portion of the intestine has been excised;

FIG. 7 is another partial cross-sectional view of the stapler of FIG. 6 with the distal end and proximal end of the intestine sewn around the anvil shaft;

FIG. 13 is a partial cross-sectional view showing the stapler of FIGS. 10-12 in the open position inserted into an intestine wherein a portion of the intestine has been excised;

FIG. 14 is another partial cross-sectional view of the stapler of FIG. 13 with the distal end and proximal end of the intestine sewed around the anvil shaft;

DETAILED DESCRIPTION

Turning to the Drawings, wherein like numerals denote like components, there is shown a circular stapler 10 that includes a unique and novel system for providing feedback to the surgeon to indicate when the instrument has cut through tissue clamped in the instrument. A variety of different circular staplers are known in the art. FIGS. 1-5 illustrate an exemplary circular stapler arrangement that may employ the benefits of various aspects of the subject invention. It is conceivable, however, that the various embodiments of the present invention may be successfully employed with other stapler constructions without departing from the spirit and scope of the present invention.

Figure 1:
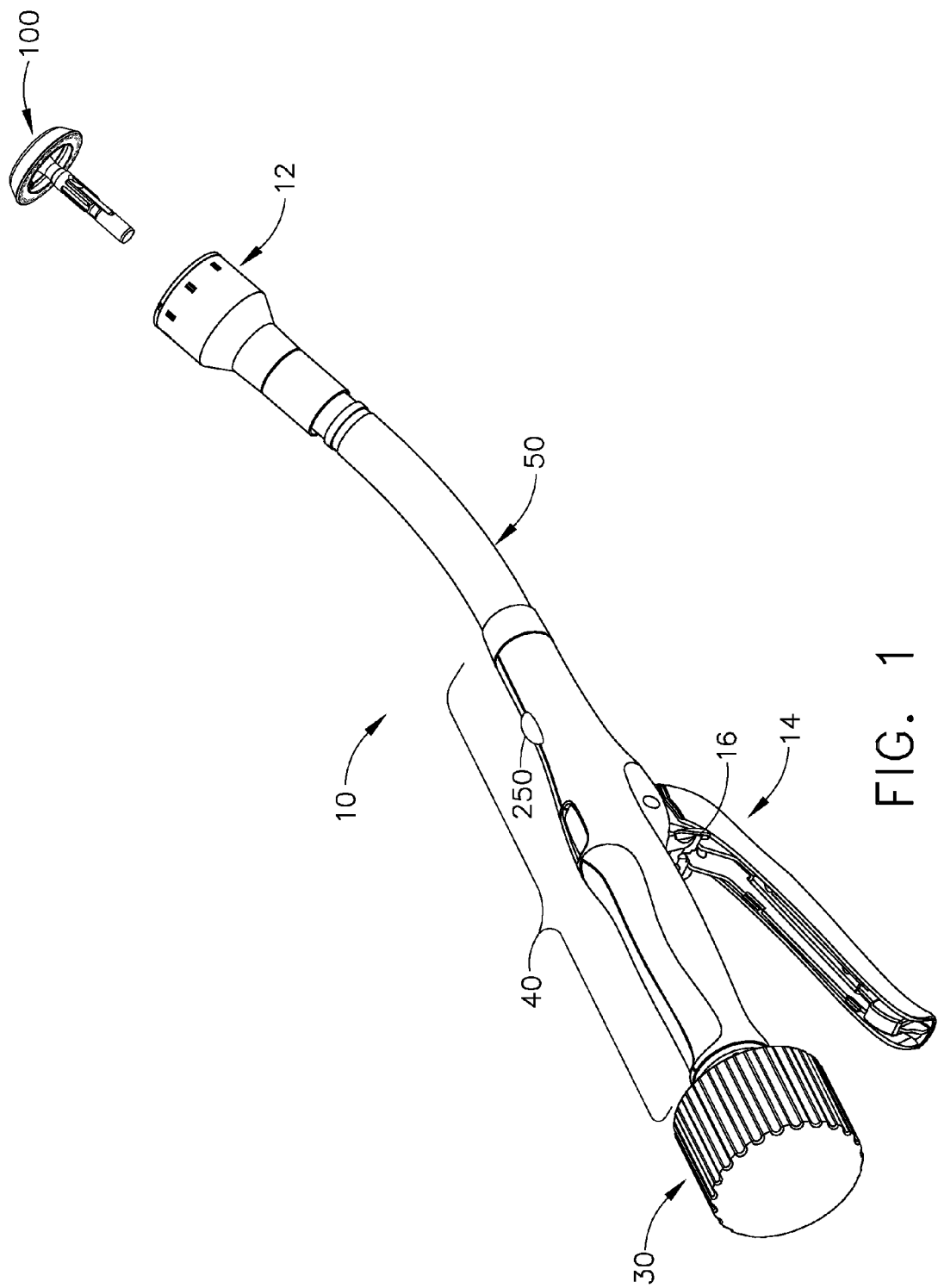
FIG. 1 is a perspective view of a surgical stapler that may be employed in connection with various embodiments of the present invention.

As seen in FIG. 1, there is disclosed a circular stapler 10 that includes a stapling head assembly 12, an anvil 100, an adjustment knob 30, and a trigger 14. The stapling head assembly 12 is coupled to a handle assembly 40 by a shaft assembly 50. The trigger 14 is pivotally supported by the handle assembly 40 and is configured to operate the stapler 10 when a safety mechanism 16 is released. When the trigger 14 is activated, a drive system operates within the shaft assembly 50 so that staples 90 (FIG. 2) are expelled from the stapling head assembly 12 into forming contact with the anvil 100. Simultaneously, a knife 70, that is operably supported within the head 12, acts to cut tissue held within the circumference of the stapled tissue. The stapler 10 is then pulled through the tissue leaving stapled tissue in its place.

Figure 2:
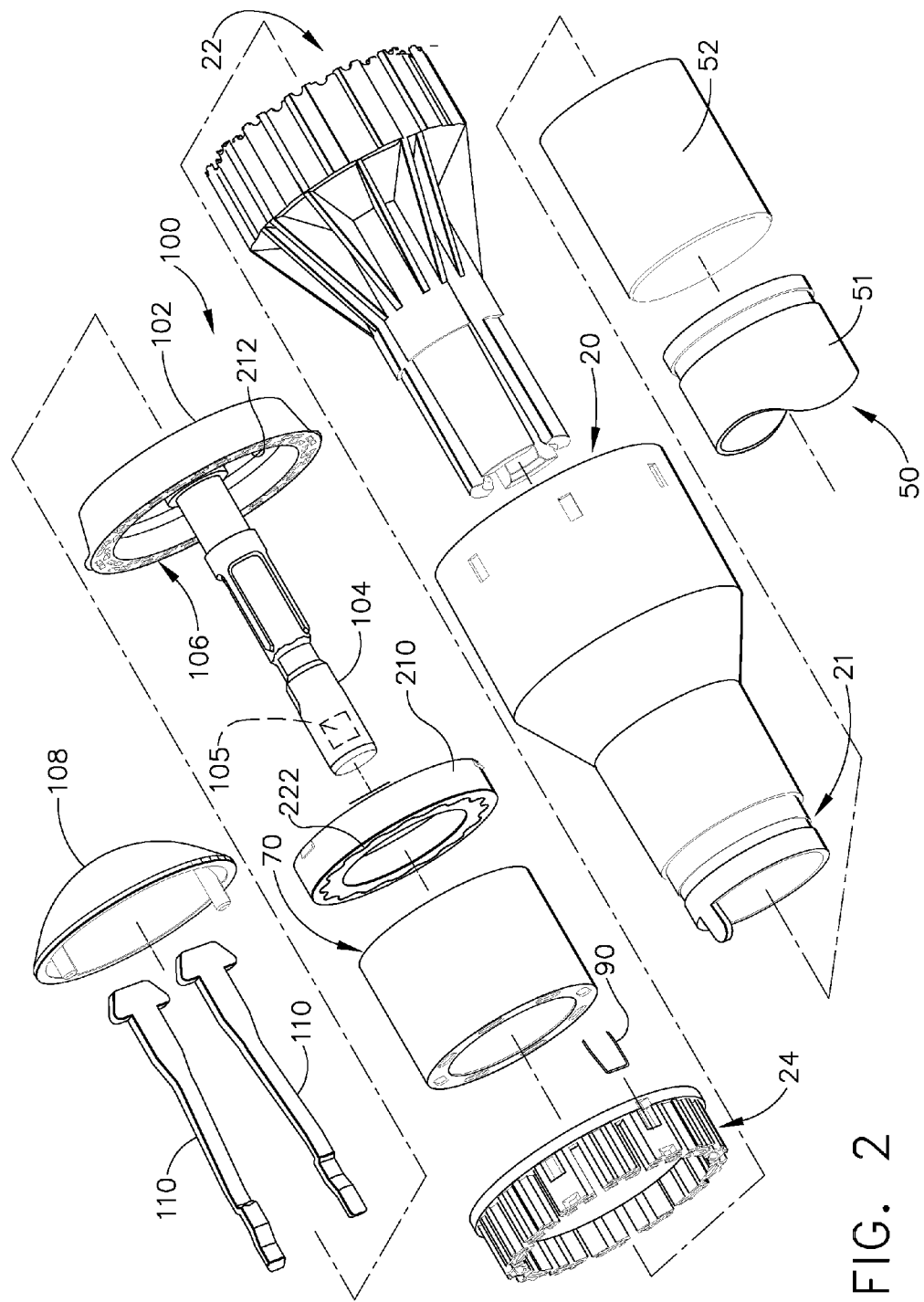
FIG. 2 is an exploded assembly view of the staple head assembly of the surgical stapler depicted in FIG. 1.
Figure 3:
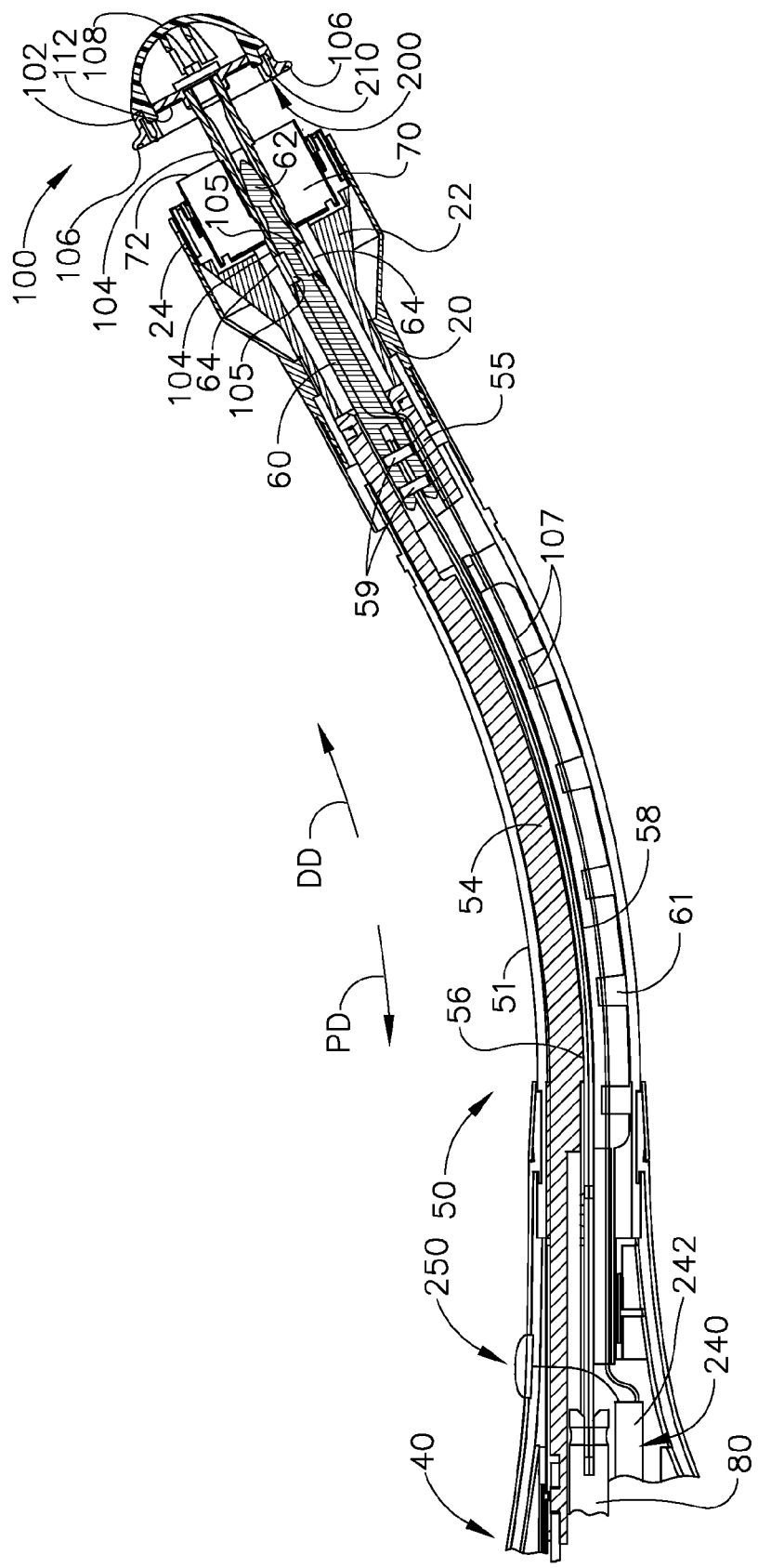
FIG. 3 is a cross-sectional view of the shaft and staple head assembly of the surgical stapler of FIG. 1.

FIGS. 2 and 3 illustrate one form of anvil 100 and stapling head assembly 12 that may be employed in connection with various embodiments of the subject invention. As can be seen in those Figures, the anvil 100 may have a circular body portion 102 that has an anvil shaft 104 for attaching a trocar 60 (FIG. 3) thereto. The anvil body 102 has a staple forming undersurface 106 thereon and may also have a shroud 108 attached to the distal end thereof. The anvil 100 may be further provided with a pair of trocar retaining clips or leaf-type springs 110 that serve to releasably retain the trocar 60 in retaining engagement with the anvil shaft 104 as will be discussed in further detail below.

As can also be seen in FIG. 2, the stapling head assembly 12 may comprise a casing member 20 that supports a cartridge supporting assembly in the form of a staple driver assembly 22 therein that is adapted to interface with a circular staple cartridge 24 and drive staples 90 supported therein into forming contact with the staple forming undersurface 106 of anvil 100. The circular knife 70 is centrally disposed within the staple driver assembly 22 and has a cutting edge 72 formed thereon. The proximal end 21 of the casing member 22 may be coupled to an outer tubular shroud 51 of the shaft assembly 50 by a distal ferrule member 52.

FIG. 3 illustrates one form of shaft assembly 50 that may be employed with various embodiments of the present invention. The shaft assembly 50 may include a compression shaft 54, a distal compression shaft portion 55, a top tension band 56, a bottom tension band 58 and a spacer band 61 that are assembled within the outer tubular shroud 51. A trocar tip 64 may be attached to the top tension band 56 and bottom tension band 58 by fasteners 59. The proximal ends of the top tension band 56 and bottom tension band 58 may be attached to a distal end of an adjustment shaft 80. As illustrated in FIG. 3, the tip 62 of the trocar 60 may be inserted into the anvil shaft 104 of the anvil 100 and retained in engagement by trocar retaining clips 110.

As can also be seen in FIG. 3, the distal compression shaft portion 55 is coupled to the staple driver assembly 22. Thus, axial movement of the compression shaft 54 within the outer tubular shroud 51 causes the staple driver assembly 22 to move axially within the casing member 20. Actuation of the firing trigger 14 will cause the compression shaft 54 to move in the distal direction (arrow "DD") thereby driving the staple driver assembly 22 distally to fire the staples 90 into forming contact with the staple forming undersurface 106 of the anvil 100. As the staple driver assembly 22 is driven distally, it also drives the cutting edge 72 of the knife 70 through the tissue held within the circumference of the stapled tissue into a knife board 210 mounted in the anvil 100.

In various embodiments, the adjustment shaft 80 is axially movably supported within a handle assembly 40 of the type and construction disclosed in U.S. Patent Publication No. US-2008-0078806-A1 to Todd Philip Omaits, et al., filed Sep. 29, 2006 that is owned by the Assignee of the present application and which is herein incorporated by reference in its entirety. However, other handle and firing system arrangements may be employed without departing from the spirit and scope of the present invention.

Figure 4:
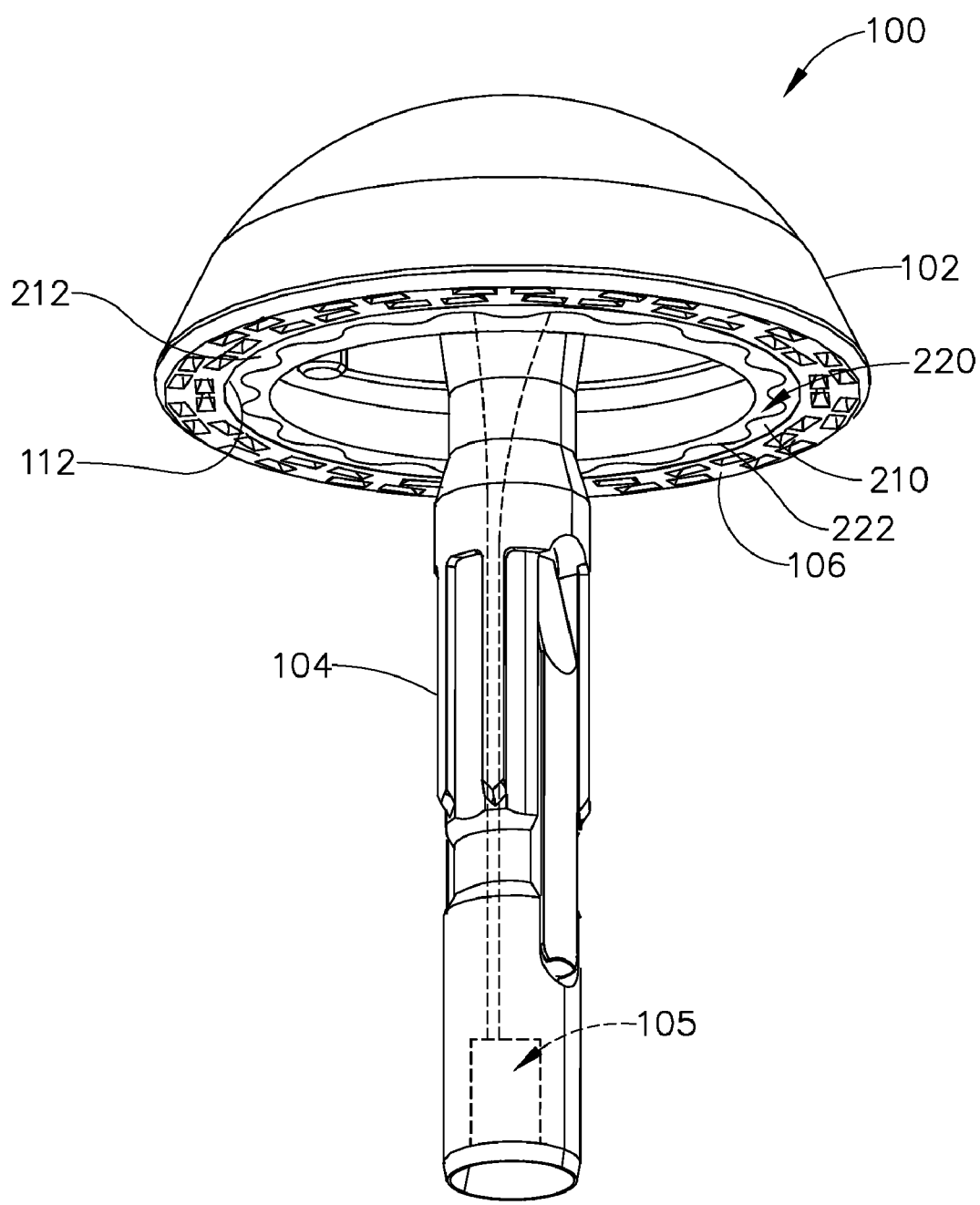
FIG. 4 is a perspective view of an anvil and knife board embodiment of the present invention.
Figure 5:
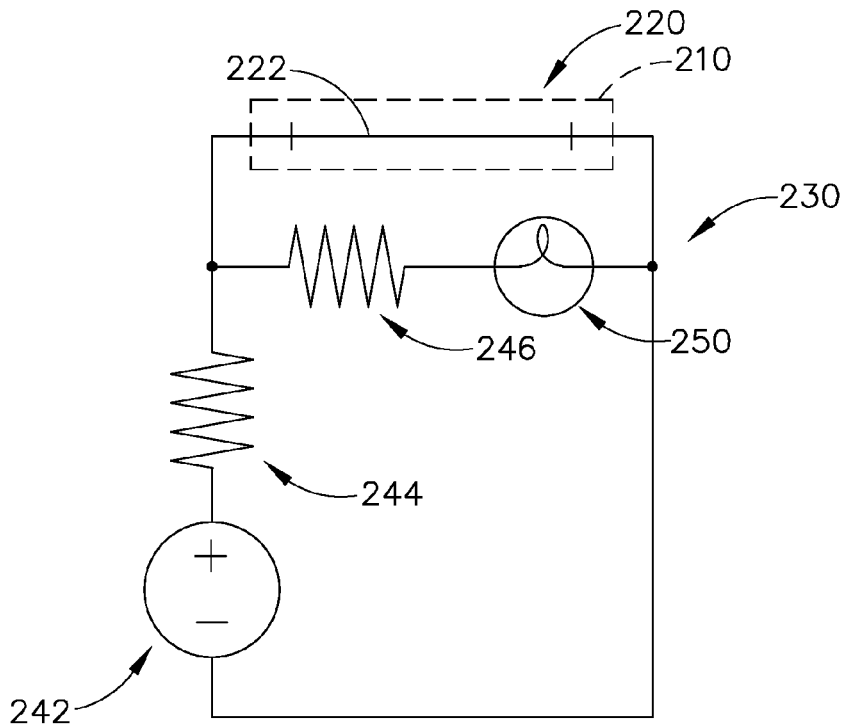
FIG. 5 is a schematic view of a travel indicator circuit embodiment of the present invention.

Various embodiments of the present invention include a unique and novel feedback system generally designated as 200 for providing an indication to the surgeon that the cutting member has cut through the tissue that has been clamped between the staple cartridge 24 and the anvil 100. One embodiment of the tissue feedback system 200 is depicted in FIGS. 3-5. For example, the feedback system 200 may include a knife board or washer 210 that may be fitted into a cavity 112 in the anvil body 102. The knife board 210 provides a solid backing surface into which the circular knife 70 may be advanced. The knife board 210 may be fabricated from plastic and have at least one sensor 220 affixed thereto to detect when the knife 210 has advanced beyond the tissue cutting position to ensure that the tissue has been cut thereby. In various embodiments, for example, the sensor 220 may comprise at least one wire 222 that is positioned on the proximal surface 212 of the knife board 210. In particular, the wire 222 may be affixed to the proximal surface 212 of the knife board 210 by glue or other suitable fastener arrangement and be so oriented thereon to "interact" with the knife 70 after the knife 70 has cut through the tissue positioned between the cutting edge of the knife 70 and the proximal surface 212 of the knife board 210. In other embodiments the at least one wire 222 may be embedded within the knife board 210.

FIG. 5 illustrates a feedback circuit 230 that may be used in connection with the sensor 220 arrangement. As can be seen in that Figure, the feedback circuit 230 may include a Direct Current ("DC") power source 240 that may comprise a battery or number of batteries 242 or other suitable DC power source. The battery 242 may be supported by the handle assembly 40 such that it may be easily installed and replaced. The feedback circuit 230 may additionally include a first resistor 244 that is connected in series with the wire or wires 222 in or on the knife board 210. In addition, a second resistor 246 is connected in series with an indicator 250. The second resistor 246 and indicator are connected in parallel to the wire(s) 222 such that the wires 222, if uncut by the knife 70, short circuit the second resistor 246 and indicator 250. In this embodiment, prior to cutting through the tissue, the current flows through the wire(s) 222 in or on the knife board 210 and little or no current flows through the indicator 250 such that it is not turned on. However, when the knife 70 severs the wire(s) 222, the current flows through the second resistor 246 and powers the indicator 250. The indicator 250 may comprise a light, a light emitting diode ("LED"), a vibration generating device, a sound generating device, etc. or a combination of such devices.

Each of the wire(s) 222 may be wired or otherwise electrically coupled to anvil contacts 105 formed on the anvil shaft 104. See FIGS. 3 and 4. The anvil contacts 105 are arranged to make electrical contact with corresponding trocar contacts 64 formed or otherwise mounted to the trocar tip 62 when the anvil body 104 is coupled to the trocar 60. The trocar contacts 64 are wired to the battery 242 and the indicator 250 that are supported in the handle assembly 40 by corresponding wires 107. Thus, when the anvil 100 is coupled to the trocar 60, a complete electrical feedback circuit 230 is formed.

One exemplary method of using the circular stapler 10 will now be described with reference to FIGS. 6-9. When performing an anastomosis using a circular stapler 10, the intestine 300 may be stapled using a conventional surgical stapler with multiple rows of staples being emplaced on either side of a target section (i.e., specimen) of intestine 300. FIG. 6 illustrates the liner staple lines 310, 320. The target section is typically simultaneously cut as the section is stapled. The target section has already been excised in FIG. 6. After removing the target specimen, the surgeon inserts the anvil 100 into the proximal portion 302 of the intestine 300, proximal of the staple line 310. This is done by inserting the anvil head 100 into an entry port cut into the proximal intestine portion 302 or the anvil 100 can be placed transanally, by placing the anvil 100 on the distal end of the stapler 10 and inserting the instrument through the rectum. Next, the surgeon attaches the anvil 100 to the trocar tip 62 of the stapler 100 and inserts the anvil 100 into the distal portion 306 of the intestine 300. The surgeon may then tie the distal end 304 of the proximal section 302 of the intestine 300 to the anvil shaft 104 using a suture 312 or other conventional tying device and also tie the proximal end 308 of the distal intestine portion 306 around the anvil shaft using another suture 314. See FIG. 7. The surgeon then begins to rotate the closure knob assembly 30 in the clockwise direction to draw the anvil 100 toward the cartridge 24 supported in the staple driver 22 to close the gap between the anvil 100 and cartridge 24 and thereby engage the proximal end 308 of the distal intestine portion 306 with the distal end 304 of the proximal intestine portion 302 in the gap "G" therebetween. See FIG. 8. The surgeon continues to rotate the closure knob assembly 30 until the desired gap G is attained. When in that position, the surgeon may then pivot the safety yoke 16 to the off position and fire the stapler 10 by depressing the firing trigger 14. Depressing the trigger 14 causes the compression shaft 54 to drive the staple driver 22 distally to drive the staples 90 to be driven through both ends 304, 308 of the intestine 300, thereby joining the portions 302 and 306 and forming a tubular pathway. Simultaneously, as the staples 908 are driven and formed, the knife 70 is driven through the intestinal tissue ends 304 and 308, cutting the ends adjacent to the inner row of staples 90. See FIG. 9.

Figure 9:
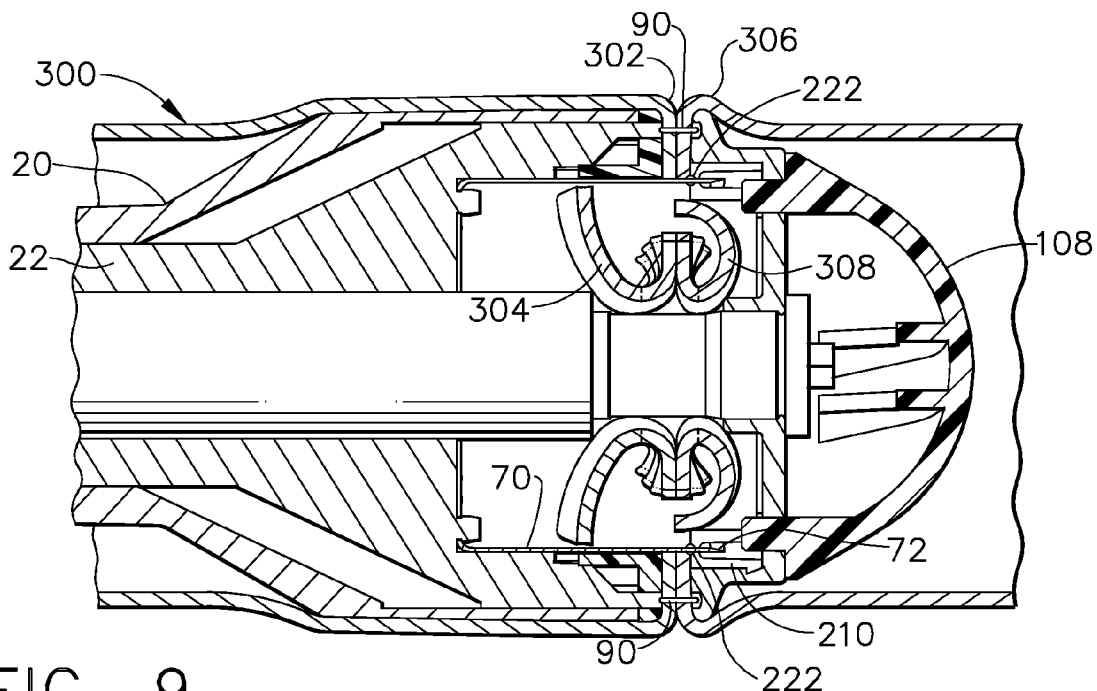
FIG. 9 is another partial cross-sectional view of the stapler of FIGS. 6-8 after it has been fired.
Figure 10:
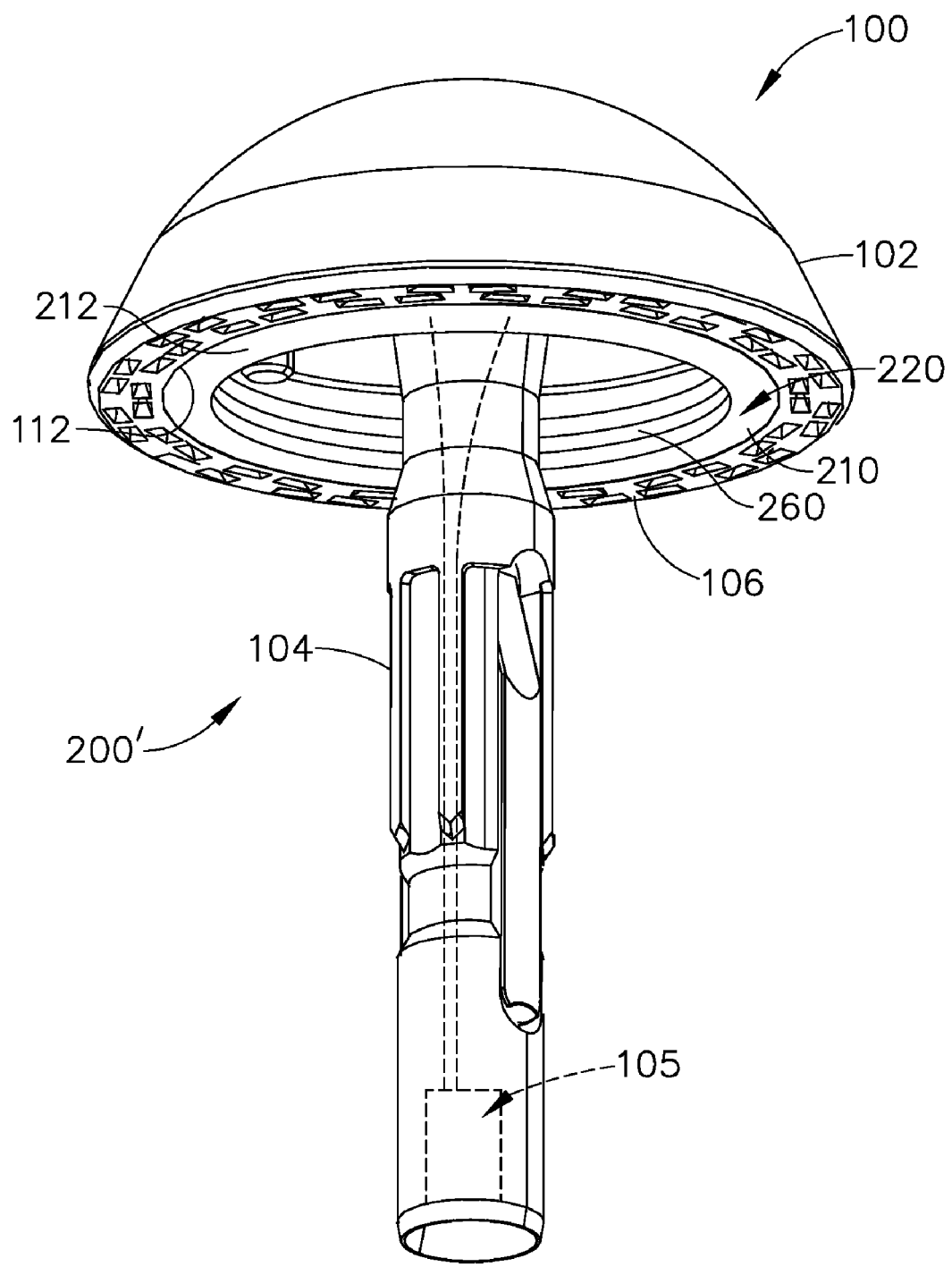
FIG. 10 is a perspective view of another anvil and knife board embodiment of the present invention.
Figure 11:
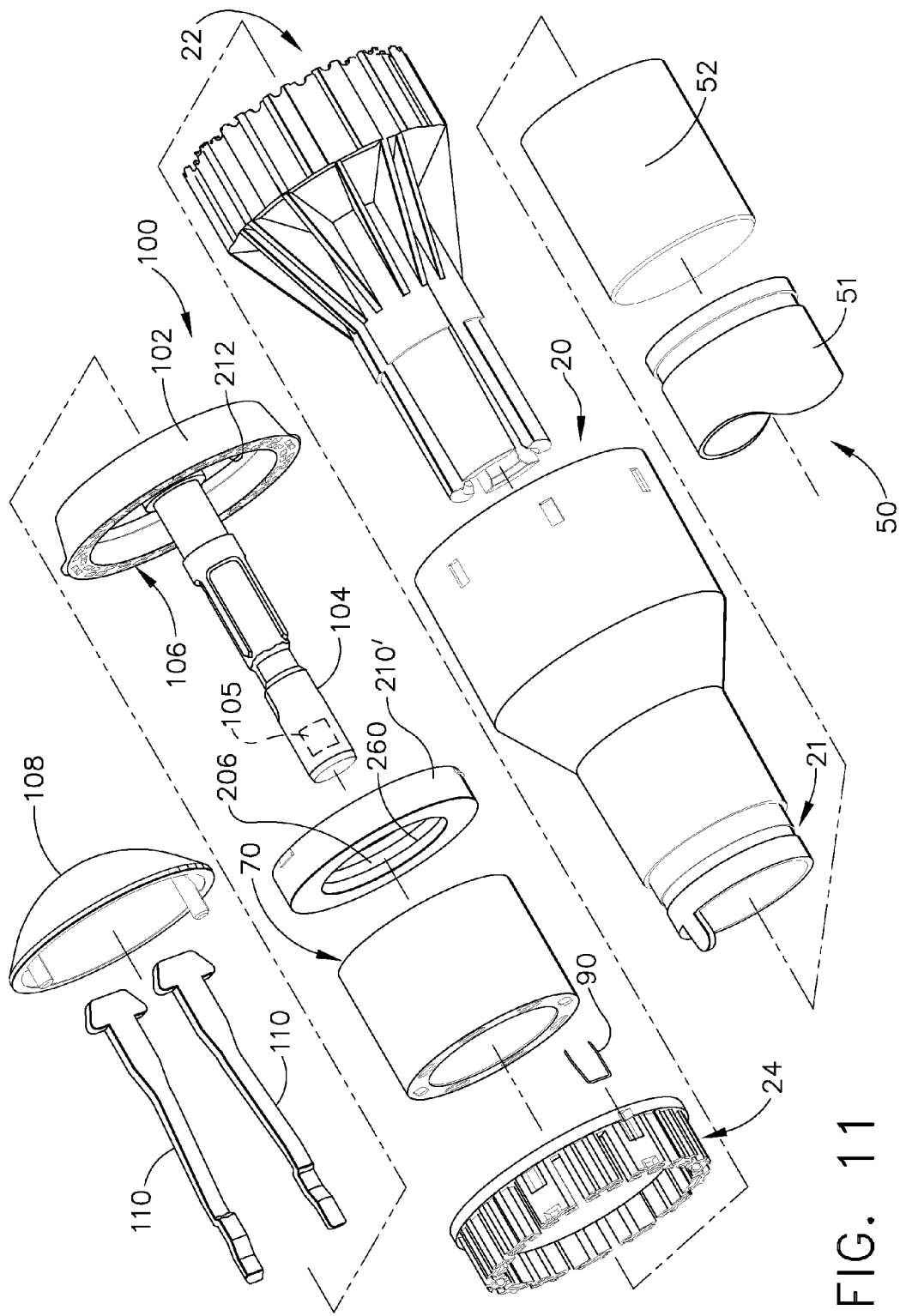
FIG. 11 is an exploded assembly view of a stapling head assembly of another surgical stapler embodiment of the present invention.
Figure 15:
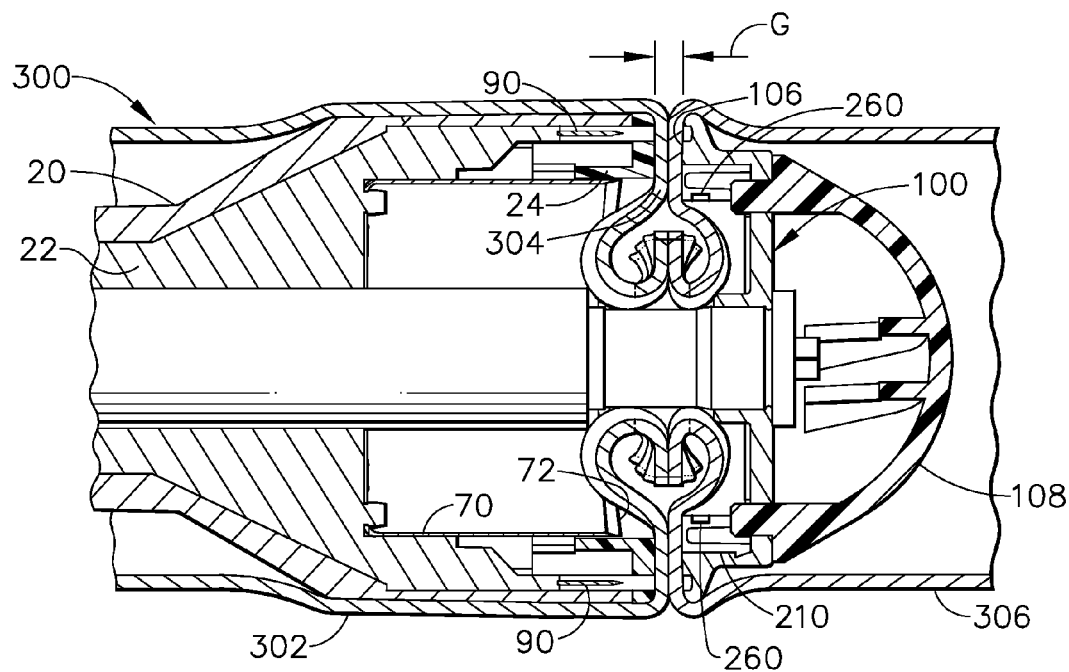
FIG. 15 is another partial cross-sectional view of the stapler of FIGS. 13 and 14 with the anvil drawn into a prefiring position.
Figure 16:
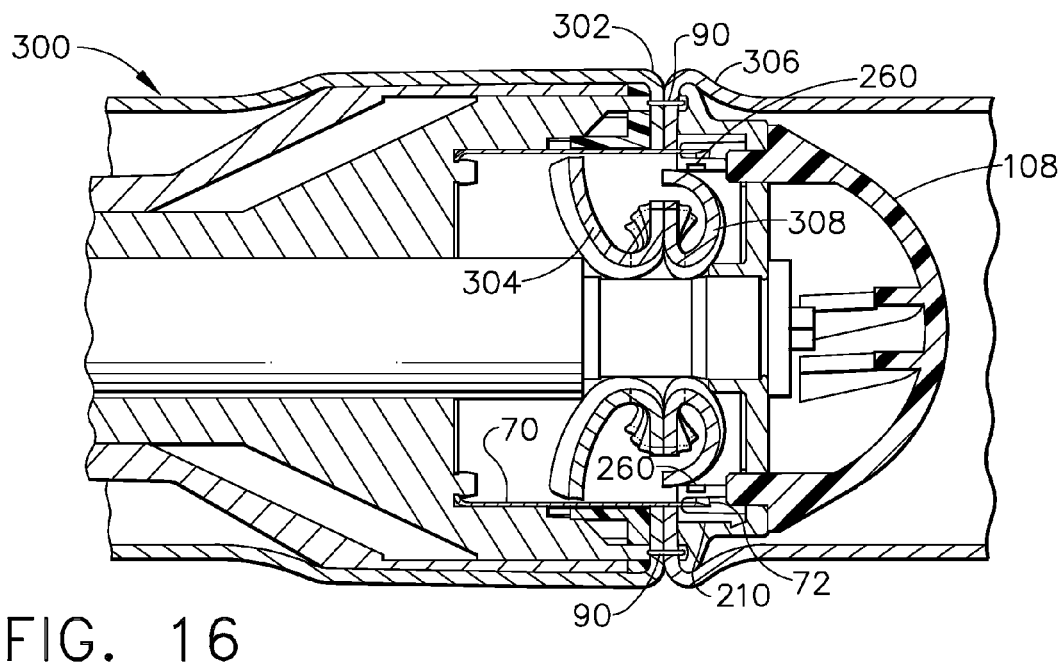
FIG. 16 is another partial cross-sectional view of the stapler of FIGS. 13-15 after it has been fired.

As can be seen in FIG. 9, as the knife 70 cuts through the tissue, the cutting edge 72 severs the wire 222 which causes an indication signal to be send to the indicator 250. That is, electrical current is permitted to flow to the indicator 250 to cause the indicator to be energized and provide an indication to the surgeon that the tissue has been severed. In an alternative embodiment, an annular cavity 214 may additionally be provided in the knife board 210. After the knife 70 has cut through the clamped tissue, the knife edge 72 may be advanced further through a wall portion 212 that covers the annular cavity 214 in the knife board 210. As the knife 70 is advanced through the wall portion 212, an audible sound may be created. In addition, the surgeon may sense some tactile vibration as the knife crunches through the wall portion 212. Therefore, such arrangement may actually provide the surgeon with an additional audible and/or tactile signal that is created when the cutting edge 72 cuts or breaks through the wall portion 212 as well as the indication (e.g., light, a second sound, vibration, etc.) provided by indicator 250.

Figure 12:
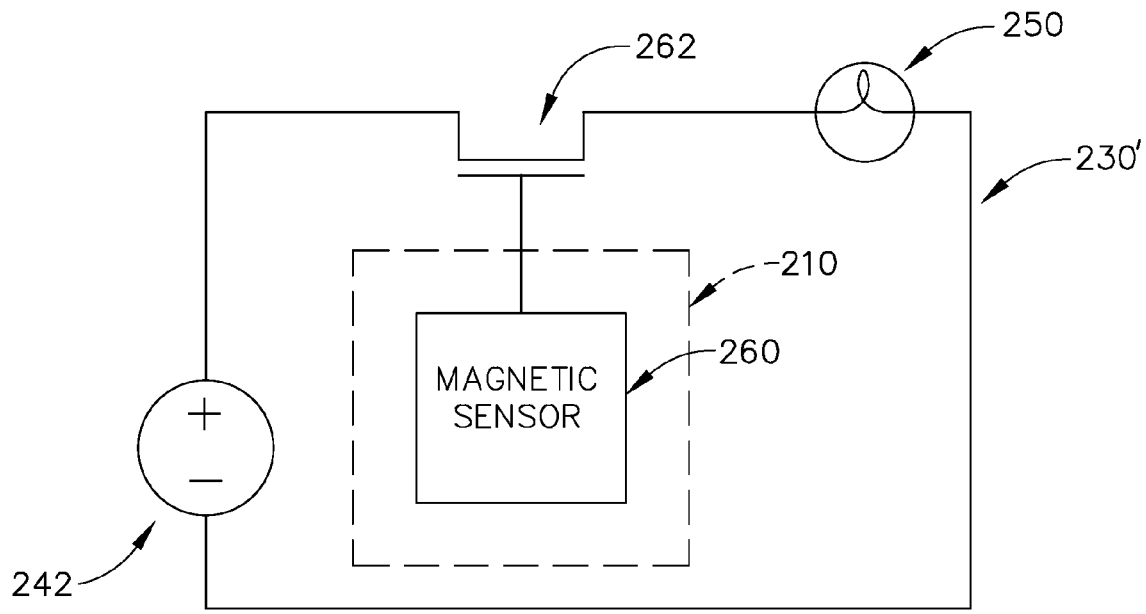
FIG. 12 is a schematic view of another travel indicator circuit embodiment of the present invention.
Figure 8:
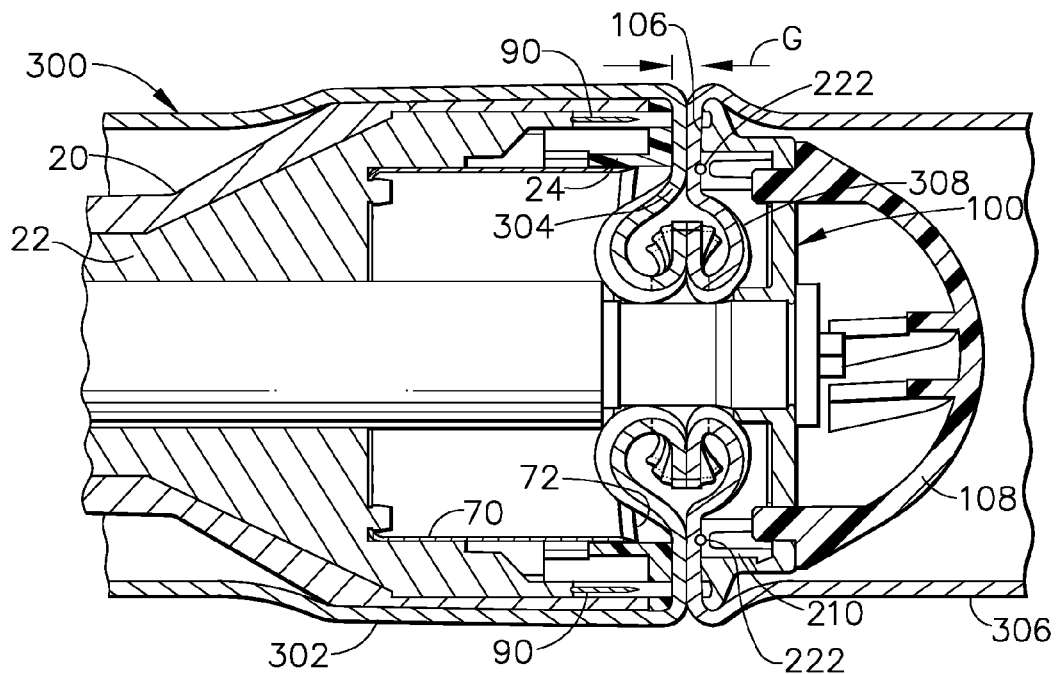
FIG. 8 is another partial cross-sectional view of the stapler of FIGS. 6 and 7 with the anvil drawn into a prefiring position relative to the stapling head assembly.

FIGS. 10-16 illustrate another feedback system 200' embodiment of the present invention. In this embodiment, for example, the sensor 220 may comprise at least one magnetic sensor 260 in the knife board 210 that is oriented to detect the knife 70 after it is cut the tissue. An exemplary circuit 230' is illustrated in FIG. 12. As can be seen in that Figure, a transistor 262 may be connected to the battery 242, the indicator 250 and the magnetic sensor 260. Until the magnetic sensor 260 detects the presence of the knife 70 after it has cut through the tissue, current is not permitted to flow to the indicator 250. However, when the magnetic sensor 260 detects the presence of the knife 70 after cutting through the tissue, current is permitted to flow to the indicator 250. The magnetic sensor 260 may be connected to the anvil contacts 105 as was described above such that when the anvil body 104 is attached to the trocar 60, the electrical circuit 230' is established.

FIGS. 13-16 illustrate operation of the indicator system 200'. As can be seen in those Figures, after the cutting edge 72 of knife 70 has cut through the tissue, it may sever a wall portion 212 that covers an annular cavity 214 formed in the knife board 210. As the knife 70 cuts through the wall portion 212, an audible sound may be created. The magnetic sensor 260 may be positioned in the wall of the knife board 210 to also detect the presence of the cutting edge 72 in the cavity 214. Thus, as discussed above, when the magnetic sensor 260 detects the knife 70, current is permitted to flow to indicator 250. Therefore, such arrangement may actually provide the surgeon with an audible signal and/or tactile signal that is created when the cutting edge 72 cuts or breaks through the wall portion 212 as well as a second indication (e.g., light, a second sound, vibration, etc.) provided by the indicator 250.

The various embodiments of the present invention represent a vast improvement over prior circular staple arrangements that only provided the audible feedback generated as the cutting knife severed or otherwise broke through a portion of the knife board. Various embodiments of the subject invention may employ multiple indicators 250 and provide multiple forms of feedback (audio, visual, vibratory, tactile). Also, in addition to the forms of sensors disclosed herein, alternative sensor arrangements may also be employed. For example, a mechanical sensor or sensors may be employed to detect the cutting edge of the knife 70. Such sensor or sensors would be mounted within the knife board or similar member, such that after the knife edge has cut through the clamped tissue, it physically contacts a portion of the mechanical sensor or sensors to cause the mechanical sensor to permit current to flow to the indicator 250.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical stapling instrument for applying one or more surgical staples to tissue, comprising:
    a handle assembly;
    a stapling head assembly operably coupled to said handle assembly by a shaft assembly, said stapling head assembly comprising:
        a staple cartridge for supporting one or more surgical staples;
        an anvil for clamping the tissue against said staple cartridge;
        a staple driver assembly for engaging and driving the staples from said staple cartridge into the tissue and against said anvil; and
        a knife movably supported in said stapling head assembly for cutting through the clamped tissue;
    a drive system for applying drive motions to said staple driver assembly and said knife; and
    a knife board supported in said anvil, said knife board supporting at least one sensor configured to transmit a signal to an indicator when said knife has cut through said clamped tissue and including a wall portion configured to be cut by said knife after cutting through said clamped tissue such that at least an audio signal or tactile signal is generated by said knife cutting through said knife board.

2. The surgical stapling instrument of claim 1 wherein said at least one sensor comprises at least one wire affixed to said knife board.

3. The surgical stapling instrument of claim 2 wherein said at least one wire is embedded in said knife board.

4. The surgical stapling instrument of claim 1 wherein said at least one sensor comprises a magnetic sensor.

5. The surgical stapling instrument of claim 1 wherein said indicator comprises an indicator selected from the group of indicators consisting of: a light generating device, a vibration generating device, and a sound generating device.

6. A method for processing an instrument for surgery, the method comprising:
obtaining the surgical stapling instrument of claim 1;
sterilizing the surgical stapling instrument; and
storing the surgical stapling instrument in a sterile container.

7. A surgical stapling instrument for applying one or more surgical staples to tissue, comprising:
a handle assembly;
a stapling head assembly operably coupled to said handle assembly by a shaft assembly, said stapling head assembly comprising:
a staple cartridge for supporting one or more surgical staples;
an anvil for clamping the tissue against said staple cartridge;
a staple driver for engaging and driving the staples from said staple cartridge into the tissue and against said anvil; and
a knife movably supported in said stapling head assembly for cutting through the clamped tissue;
a drive system for applying drive motions to said staple driver and said knife; and
a feedback system comprising a knife board mounted in said anvil, said knife board having at least one sensor operably supported therein for detecting the presence of said knife after said knife has cut through said clamped tissue, said sensor operably communicating with an indicator supported by said handle assembly such that when said knife has cut through said clamped tissue, said sensor permits said indicator to be energized.

8. The surgical stapling instrument of claim 7 wherein said sensor comprises at least one wire on said knife board and wherein said at least one indicator comprises at least one light emitting diode mounted on said handle assembly.

9. The surgical stapling instrument of claim 7 wherein said at least one sensor comprises at least one wire affixed to said knife board.

10. The surgical stapling instrument of claim 9 wherein said at least one wire is embedded in said knife board.

11. The surgical stapling instrument of claim 7 wherein said at least one sensor comprises a magnetic sensor.

12. The surgical stapling instrument of claim 7 wherein said indicator comprises an indicator selected from the group of indicators consisting of: a light generating device, a vibration generating device, and a sound generating device.

13. The surgical stapling instrument of claim 7 wherein said feedback system is configured to provide at least one other form of feedback when said knife has cut through said clamped tissue.

14. The surgical stapling instrument of claim 13 wherein said at least one other form of feedback comprises tactile feedback which can be felt by grasping said handle assembly.

15. The surgical stapling instrument of claim 13 wherein said at least one other form of feedback comprises an audio feedback.

16. A method for processing an instrument for surgery, the method comprising:
obtaining the surgical stapling instrument of claim 7;
sterilizing the surgical stapling instrument; and
storing the surgical stapling instrument in a sterile container.

17. A surgical stapling instrument for applying one or more surgical staples to tissue, comprising:
a handle assembly;
a stapling head assembly comprising:
a staple cartridge for operably supporting a plurality of staples therein;
a staple driver for engaging and driving staples from said staple cartridge;
a knife movably supported in said stapling head assembly;
a drive system for applying drive motions to said staple driver and said knife;
a shaft assembly operably coupled to said handle assembly and said stapling head assembly, said shaft assembly including a selectively movable trocar;
an anvil detachably mounted to said trocar and positioned relative to said stapling head assembly, such that at least some of said tissue may be clamped between said staple cartridge and said anvil, said anvil having a body portion and a stem protruding from said body portion, said stem configured to operably receive a tip portion of said trocar therein; and
a feedback system comprising at least one sensor supported by said anvil, said anvil stem being configured to establish an electrical connection between said at least one sensor and at least one indicator supported by said handle assembly when said tip portion of said trocar is seated within said anvil stem, such that when said knife has cut through said clamped tissue, said at least one sensor permits said indicator to be energized.

18. The surgical instrument of claim 17 further comprising a knife board supported in said body portion of said anvil, said knife board operably supporting said at least one sensor therein.

19. The surgical instrument of claim 18 wherein said knife board is configured to generate an audible sound apart from said signal when said knife is advanced through a portion of said knife board.

20. The surgical stapling instrument of claim 17 wherein said indicator comprises an indicator selected from the group of indicators consisting of: a light generating device, a vibration generating device, and a sound generating device.

21. The surgical stapling instrument of claim 17 wherein said feedback system is configured to provide at least one other form of feedback when said knife has cut through said clamped tissue.

22. A method for processing an instrument for surgery, the method comprising:
obtaining the surgical stapling instrument of claim 18;
sterilizing the surgical stapling instrument; and
storing the surgical stapling instrument in a sterile container.

* * * * *